United States Patent [19]

Christensen

[11] Patent Number: Plant 5,693

[45] Date of Patent: Mar. 18, 1986

[54] HYBRID TEA ROSE PLANT CV. AROLALA

[75] Inventor: Jack E. Christensen, Ontario, Calif.

[73] Assignee: Armstrong Nurseries, Inc., Ontario, Calif.

[21] Appl. No.: 624,511

[22] Filed: Jun. 25, 1984

[51] Int. Cl.[4] ..... A01H 5/00

[52] U.S. Cl. ..... Plt./11

[58] Field of Search ..... Plt./11

*Primary Examiner*—Robert E. Bagwill

*Attorney, Agent, or Firm*—Synnestvedt & Lechner

[57] ABSTRACT

A new hybrid tea rose for cut flower production and garden decoration, having as its seed parent an undisseminated seedling from the cross [Angel Face (U.S. Plant Pat. No. 2,792) × First Prize (U.S. Plant Pat. No. 2,774)] and as its pollen parent Lady X (U.S. Plant Pat. No. 2,691). The new cultivar produces an abundance of well-formed flowers having a blended lavender coloration, borne on strong stems of cutting length. The petals are of heavy substance and hold up well in varying climates. The new variety is an attractive, upright plant of medium height with vigorously growing, deep green foliage.

1 Drawing Figure

This invention relates to a new variety of hybrid tea rose cv. Arolala. The plant is a half-hardy outdoor seedling of the medium-height bush type, cultivated for garden decoration. It was discovered by Jack E. Christensen in Ontario, Calif., and has as its seed parent an undisseminated seedling of the cross [Angel Face (U.S. Plant Pat. No. 2,792) × First Prize (U.S. Plant Pat. No. 2,774)], and as it pollen parent, Lady X (U.S. Plant Pat. No. 2,691).

The new variety cv. Arolala may be distinguished from other presently available commercialized rose cultivars by the following combination of characteristics: the blended lavender coloration of its flowers, essentially as described and illustrated herein; its abundant production of large, well-formed flowers on strong stems suitable for cutting; its vigorous growth; its attractive bush of medium height and upright habit; its abundance of deep green foliage; and its heavy petal substance that holds up well in varying climates. Arolala holds these distinguishing characteristics through succeeding propagations by budding.

The new rose may be distinguished from its seed parent, an undisseminated seedling of the cross Angel Face × First Prize, by the following combination of characteristics: Whereas the seed parent produces bicolor flowers of lavender pink with a reverse of ivory, the new cultivar produces flowers of a blended medium lavender coloration, essentially as described and illustrated herein. Arolala produces a mature bush of sturdy, upright habit and medium height, whereas the seed parent produces a mature bush with a lower, more spreading habit. Whereas the seed parent produces growth with an abundance of many-sized prickles, the new cultivar produces growth with significantly fewer prickles which are predominantly of one size.

Arolala may be distinguished from its pollen parent, Lady X, by the following combination of characteristics: Arolala produces flowers of a medium lavender coloration with some blushing to deeper colors in the bud stage, essentially as described and illustrated herein, whereas Lady X produces flowers of a significantly lighter and more uniform lavender coloration. The new cultivar produces an upright mature bush of medium height, whereas Lady X produces a significantly taller, more open mature bush. Lady X produces flowers whose petals reflex back quite heavily as the bloom opens, whereas Arolala produces flowers whose petal edges exhibit considerably less reflexing as the bloom matures.

The accompanying drawing illustrates the plant in color and shows the flowering thereof from bud to full bloom. Throughout this specification, color names beginning with a small letter signify that the name of that color as used in common speech is aptly descriptive. Color names beginning with a capital letter designate values based upon The R.H.S. Colour Chart of The Royal Horticultural Society in London, England.

The descriptive matter which follows pertains to roses of the new variety grown in the environment of southern California and is believed to be applicable to similar conditions of soil and climate elsewhere.

FLOWER

The new variety usually bears its flowers singly, sometimes two or three flowers per stem, in irregular, rounded clusters. Flowers are borne on strong stems that are medium to long in length for the class. Outdoors, the plant blooms nearly continuously and in abundant quantities during the growth season. It has a slight, spicy fragrance.

BUD

The peduncle is average to long in length for the class, of average to heavy caliper, strong and erect. It is usually smooth, with some stipitate glands, and between Yellow-Green 144A and Green 136A in coloration.

Before the calyx breaks, the bud is medium to large in size for the class and of medium length, pointed and ovoid in form, with a few stipitate glands on its surface. There are usually slender foliaceous parts extending beyond the tip of the bud, equal to one quarter or more of its length.

As the calyx breaks, bud color is between Red-Purple 59A and Greyed-Purple 187A.

The inner surface of the sepals has a fine, woolly tomentum; margins are lined with hairs.

As the first petal opens, the bud is average to large in size for the class, medium to long in length, and pointed to ovoid to urn-shaped in form. On the outside of the newly-opening petals is a small basal attachment zone of near Yellow 2B in color which quickly suffuses to between Red-Purple 60D and Red-Purple 63B. Inside, the petals display a large basal attachment zone near Yellow 2B in color which slowly suffuses to between Red-Purple 60D and Red-Purple 63B; the petal edges sometimes blush to near Red-Purple 59B. The bud opens up well and is not prevented from opening by cold, hot or dry weather.

BLOOM

When fully open, the bloom is average to large in size for the class, ranging from 4½ to 5 inches in diameter. Petalage is double, with petals arranged regularly; there are from 28 to 35 petals present and from 1 to 3 petaloids. When half open, the bloom is very high-centered in form, and the petals are moderately spiraled with edges moderately reflexed outward. When fully open, the bloom is moderately cupped with loosely cupped petals and petal edges slightly reflexed outward.

The petals are of moderately heavy substance and of medium thickness, with insides slightly velvety and outsides slightly shiny. The outside petals are nearly round to broadly obovate in shape with rounded apices. The intermediate petals are broadly obovate with rounded apices. The inside petals are obovate and have rounded apices. Petal colors may be modified by being bordered or margined or shaded or washed or tinted with other colors.

The paragraph immediately following describes the color values observed in a newly opened flower on a plant grown outdoors in Ontario, Calif., in the month of October.

The outside surface of the outside, intermediate and inner petals has a small basal attachment zone near Yellow 2B in color, with the remainder of the petal quickly suffusing to between Red-Purple 68D and Red-Purple 70D. The inside surface of the outside petals has the same color as the outside surface described above, except that petal edges sometimes blush to near Red-Purple 59B. The inside surface of the intermediate and inner petals has the same coloration as the inside surface of the outside petals without blushing.

The paragraph immediately following describes the color values observed in a bloom which has been open for three days in the month of October. The plant described had been grown outdoors in Ontario, Calif.

The outside and inside surface of the outside and inside petals has a small basal attachment zone near Yellow 4D, and the remainder of the petal quickly suffuses to between Red-Purple 69B and Red-Purple 73D.

The general color effect of the newly opened flower is between Red-Purple 68D and Red-Purple 70D, with occasional blushing to near Red-Purple 59B at the outer petals. After being open three days, the bloom gives a general color effect of between Red-Purple 69B and Red-Purple 73D. The petals usually drop off cleanly and are not particularly affected by cold, hot or dry weather.

In October, flowers from plants of the new variety grown in the garden last on the bush from 3 to 4 days; flowers cut from plants grown outdoors will last from 4 to 5 days at living-room temperatures.

REPRODUCTIVE ORGANS

Stamens are many in number and are arranged irregularly about the pistils, with a few tucked in the calyx. The filaments are medium to long in length, and most have anthers. The anthers are medium to large in size, all opening approximately at once. Anther color is near Yellow 9C when immature and near Greyed-Orange 165A at maturity. Pollen is moderate to abundant in quantity and near Yellow 8B in color.

There are many pistils (approximately 85). The styles are uneven, average to long in length, of thin to average caliper, and somewhat loosely bunched. The stigma is near Yellow 4C in color. Most of the ovaries are enclosed in the calyx.

Hips are of average length and globular in shape, of a color near Orange 25A. The hips are very smooth with thick, fleshy walls.

Sepals fall soon.

Seeds are average in number (8 to 11) for the class and are medium to large in size.

FOLIAGE

The compound leaves are borne in abundant quantities and usually comprise from three to five leaflets. The leaves are of medium size for the class, moderately heavy and semi-glossy. The leaflets are nearly oval in shape, with acute apices and round to acute bases; their margins are irregularly serrate.

The upper surface of the young foliage is darker than near Greyed-Purple 187A in color; its under surface is near Greyed-Purple 187B. The upper surface of the mature foliage is between Yellow-Green 147A and Green 131A in color; its under surface is between Yellow-Green 147B and Green 136C.

The rachis is of average size, grooved on its upper side, and has a few stipitate glands on its edges. The under side of the rachis is moderately smooth.

Stipules are medium in length, medium to wide in width, and have medium to long points turning out at an angle of usually less than 90°.

The plant displays an average resistance to mildew, rust and blackspot as compared to other commercial varieties grown under comparable conditions in Ontario, Calif.

GROWTH

The plant is of medium height, much branched, and bushy and upright in habit. It displays vigorous growth. The canes are of medium caliper for the class.

The main stems are between Yellow-Green 146C and Green 136C in color. They bear few to several large prickles which are of medium length for the class. The large prickles are almost straight with broad to round bases of medium length. Prickle color is near Greyed-Yellow 161A. There are no small prickles or hairs on the main stems.

The branches are of a color between Yellow-Green 146A and Green 136A. They bear several large prickles of medium length for the class. The prickles are almost straight, with broad to round bases of medium length, and near Greyed-Orange 165C in color. The branches have no hairs and no small prickles.

New shoots are of the same color as the branches, washed heavily with near Greyed-Purple 187A. They bear several large prickles of medium length for the class, which are almost straight with medium-length, broad to round bases. Prickle color is near Greyed-Purple 187B. There are no small prickles and no hairs.

I claim:

1. A new and distinct variety of rose plant of the hybrid tea class, substantially as herein shown and described, being particularly characterized by the blended lavender coloration of its flowers, essentially as described and illustrated herein; its abundant production of large, well-formed flowers on strong stems suitable for cutting; its vigorous growth; its attractive bush of medium height and upright habit; its abundance of deep green foliage; and its heavy petal substance that holds up well in varying climates.

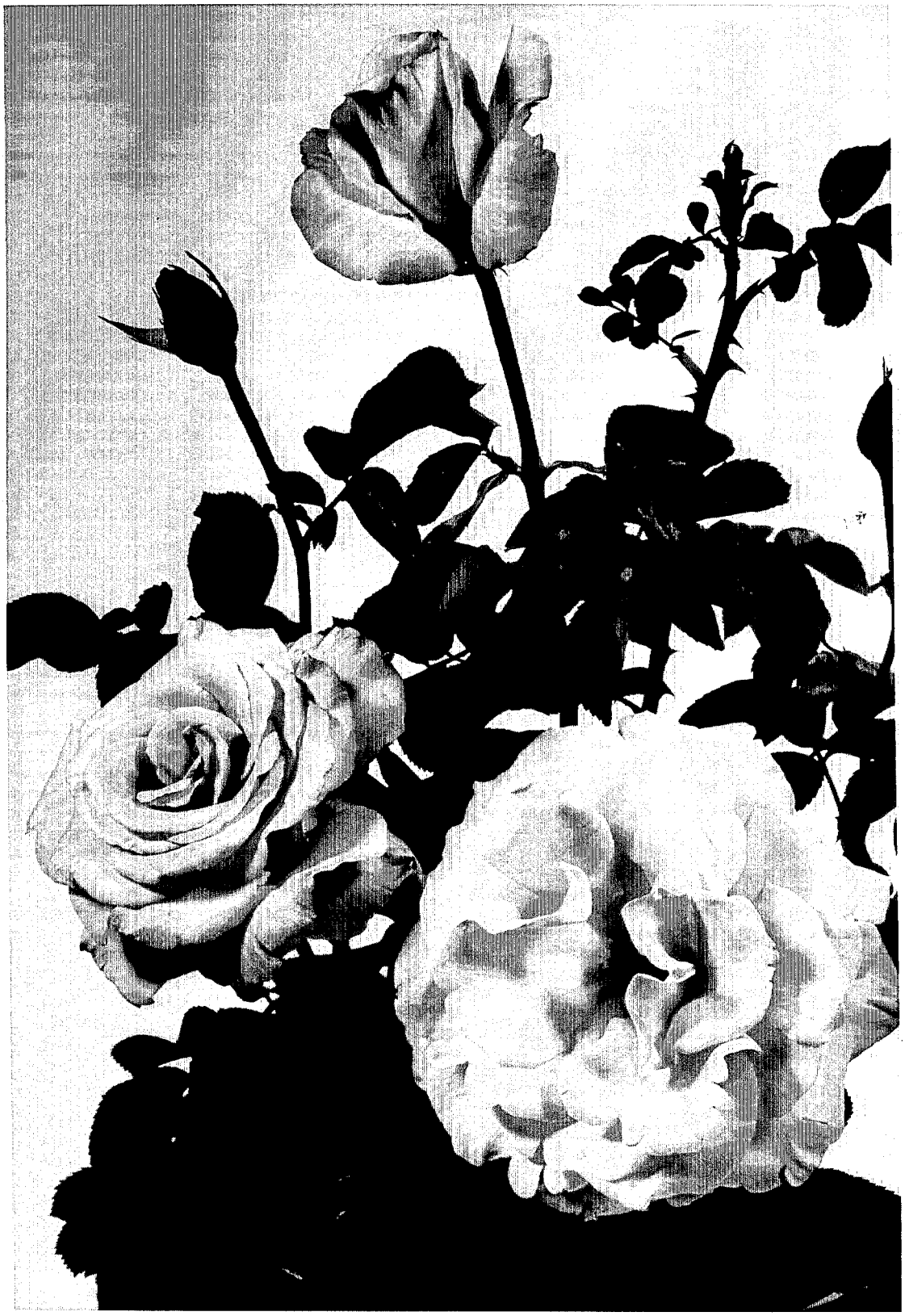

* * * * *